United States Patent [19]

Williamson et al.

[11] Patent Number: 4,997,755
[45] Date of Patent: Mar. 5, 1991

[54] HMG-COA REDUCTASE INHIBITORS PRODUCED BY NOCARDIA SP. (MA 6455)

[75] Inventors: Joanne M. Williamson, Cranford, N.J.; David Houck, Los Alamos, N. Mex.; Edward S. Inamine, Rahway, N.J.

[73] Assignee: Merck & Co., Inc., Rahway, N.J.

[21] Appl. No.: 181,877

[22] Filed: Apr. 14, 1988

[51] Int. Cl.[5] .......................... C12P 17/06; C12P 7/02; C12P 33/06; C12N 1/20
[52] U.S. Cl. .................................... 435/125; 435/155; 435/58; 435/872; 435/253.2; 435/135; 435/146; 435/148
[58] Field of Search .............. 435/253.2, 156, 125, 435/872, 146, 52, 53, 58, 117, 123, 155

[56] References Cited

U.S. PATENT DOCUMENTS

| | | | |
|---|---|---|---|
| 4,444,784 | 4/1984 | Hoffman et al. | 514/460 |
| 4,448,979 | 5/1984 | Terahara et al. | 549/292 |
| 4,517,373 | 5/1985 | Terahara et al. | 549/292 |
| 4,537,859 | 8/1985 | Terahara et al. | 435/146 |

FOREIGN PATENT DOCUMENTS 0251625  1/1988  European Pat. Off. ............ 549/292

OTHER PUBLICATIONS

Lee, S. S., and Sih, C. J. 1967, "Mechanism of Steroid Oxidation by Microorganisms," *Biochemistry* vol. 6, pp. 1395–1403.

Raymond, R. L., et al. 1967, "Microbial Hydrocarbon Co-Oxidation," *Applied Microbiology*, vol. 15, pp. 857–865.

*Primary Examiner*—Richard A. Schwartz
*Assistant Examiner*—Mary Mosher
*Attorney, Agent, or Firm*—Melvin Winokur; Joseph F. DiPrima

[57] ABSTRACT

A microbiological process is described for the preparation of 6-desmethyl-6-β-hydroxymethyl and 6-desmethyl-6-β-carboxylovastatin derivatives and 8-acyl analogs thereof.

9 Claims, No Drawings

HMG-COA REDUCTASE INHIBITORS PRODUCED BY NOCARDIA SP. (MA 6455)

BACKGROUND OF THE INVENTION

Hypercholesterolemia is known to be one of the prime risk factors for atherosclerosis and coronary heart disease, the leading cause of death and disability in western countries. The bile acid sequestrants seem to be moderately effective as antihypercholesterolemic agents but they must be consumed in large quantities, i.e., several grams at a time, and they are not very palatable.

Mevacor® (lovastatin), now commercially available, is one of a group of very active antihypercholesterolemic agents that function by limiting cholesterol biosynthesis by inhibiting the enzyme, HMG CoA reductase. In addition to the natural fermentation products, mevastatin and lovastatin, there are a variety of semi-synthetic and totally synthetic analogs thereof. For example, simvastatin wherein the 8-acyl moiety is 2,2-dimethylbutyryl is an even more potent HMG CoA reductase inhibitor than lovastatin.

The naturally occurring compounds and their semi-synthetic analogs have the following general structural formulae:

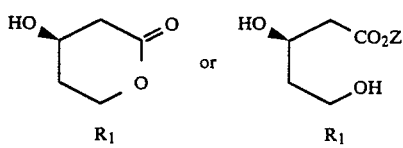

wherein: Z is hydrogen, $C_{1-5}$ alkyl or $C_{1-5}$ alkyl substituted with a member of the group consisting of phenyl, dimethylamino, or acetylamino; and $R_1$ is:

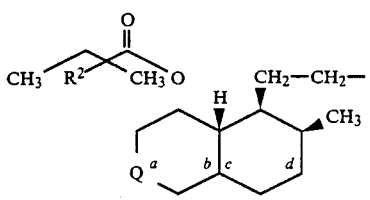

wherein Q is

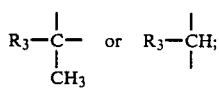

$R_3$ is H or OH; and $R_2$ is hydrogen or methyl; and a, b, c, and d represent optional double bonds, especially where b and d represent double bonds or a, b, c, and d are all single bonds, provided that when a is a double bond, Q is

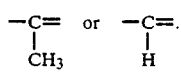

U.S. Pat. No. 4,517,373 discloses semi-synthetic hydroxy containing compounds represented by the above general formula wherein $R_1$ is

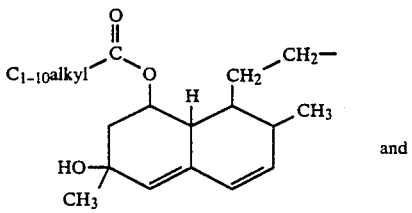

and

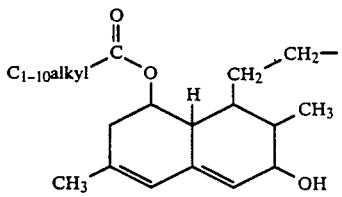

U.S. Pat. No. 4,537,859 and U.S. Pat. No. 4,448,979 also disclose semi synthetic hydroxy-containing compounds represented by the above general formula wherein $R_1$ is

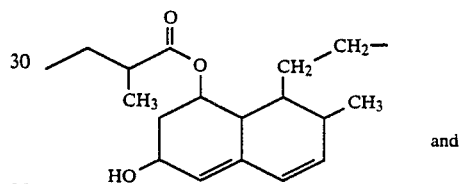

and

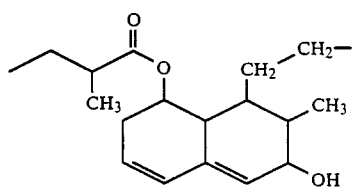

These compounds are prepared by the action of certain microorganisms on the corresponding non-hydroxylated substrates. One such organism described in U.S. Pat. No. 4,537,859 is of the genus Nocardia.

Copending U.S. patent application Ser. No. 048,136 filed May 15, 1987 discloses HMG-CoA reductase inhibitors which include 6-desmethyl-6-hydroxymethyl- and 6-desmethyl-6-carboxylovastatin analogs. These compounds were formed by bioconversion of the sodium salt of lovastatin, or analogs having a 6-methyl group, using strains of the microorganism Nocardia autotrophica (MA 6180 and MA 6181). However, the bioconversion with this microorganism gave relatively low yields of the 6-hydroxymethyl analogs.

In the instant invention the novel microorganism Nocardia sp., (MA 6455) gives an improved yield of the 6-hydroxymethyl derivative.

DETAILED DESCRIPTION OF THE INVENTION

The instant invention is a novel process for the preparation of 6-desmethyl-6-8-hydroxymethyl and 6-desmethyl-6β-carboxy derivatives of lovastatin and analogs thereof (I) using a novel microorganism of the genus Nocardia sp. (MA6455) (ATCC 53695). The substituent at the 6-position has the β configuration.

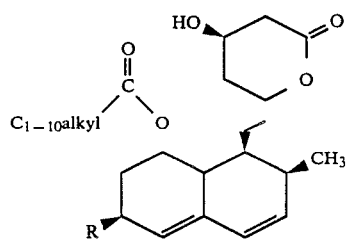

wherein R=CH₂OH or COOH.

The process involves the bioconversion of substrate (II) with the microorganism of the genus Nocardia sp. (MA6455).

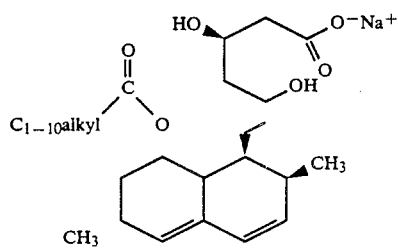

The acyl moiety

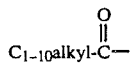

can be branched or straight, preferably it is 2-methylbutyryl or 2,2-dimethylbutyryl.

The characteristics of microorganism Nocardia sp. (MA 6455) (ATCC 53695) are described below:

Cultural Characteristics

Yeast extract-malt extract agar (ISP Medium 2)
  V: Reverse - reddish brown
  A: Moderate, powdery, flesh pink (5ca)
  SP: Reddish-brown
Oatmeal agar (ISP Medium 3)
  V: Reverse - brown to reddish brown
  A: Moderate, powdery, light rose beige (5cb)
  Sp: Reddish-brown
Inorganic salts-starch agar (ISP Medium 4)
  V: Reverse - tan becoming pinkish-tan to reddish brown
  A: Moderate, powdery, flesh pink (5ca) with edges showing a more yellowish tone.
  SP: Reddish-brown
Glycerol asparagine agar (ISP Medium 5)
  V: Reverse - tan mixed with reddish-brown
  A: Moderate, powdery, flesh pink (5ca)
  SP: Reddish-brown
Peptone iron-yeast extract agar (ISP Medium 6)
  V: Cream-colored to tan
  A: Sparse, whitish
  SP: None
  Melanin: Negative
Tyrosine Agar (ISP Medium 7)
  V: Reverse - reddish-brown
  A: Moderate, powdery, flesh pink (5ca)
  SP: Reddish-brown
Czapek-Dox Agar
  V: Reverse - yellowish-tan
  A: Moderate, cream-colored
  SP: None (V=vegetative growth; A=aerial mycelium; SP=soluble pigmet)

Morphological Characteristics

Hyphae form branching filaments with no apparent sporulation. As culture ages, aerial hyphae show a "beading"0 effect—dense areas separated by clear areas—and some fragmentation.

Chemotaxonomy

Arabinose, galactose, and meso-diaminopimelic acid are present in whole cell hydrolysates.

Physiological and Biochemical Characteristics

Oxygen requirements (Stab culture in yeast extract-dextrose+salts agar) Aerobic

Carbon Utilization: (as determined in a Pridham-Gottlieb basal medium (ISP Medium 9)+1% carbon source)

+=growth; ±=growth poor or questionable;
 −=no growth as compared to negative control (no carbon source)

| Glucose | + | Mannitol | + |
|---|---|---|---|
| Arabinose | + | Mannose | + |
| Cellulose | − | Raffinose | + |
| Fructose | + | Rhamnose | + |
| Inositol | + | Sucrose | + |
| Lactose | + | Xylose | + |
| Maltose | + | | |

Temperature range (Yeast extract-dextrose+salts agar)
  28° C. - Good vegetative growth and aerial mycelium
  37° C. - Poor vegetative growth; no aerial mycelium
  42° C. - No growth
  50° C. - No growth
All readings taken after three weeks at 28° C. unless noted otherwise. pH of all media approximately neutral (6.8–7.2).

A deposit of Nocardia sp. (MA6455) has been made under the Budapest Treaty. The deposited culture designated ATCC 53695 is available in the permanent culture collection of the American Type Culture Collection at 12301 Parklawn Drive, Rockville, MD 20852.

The compounds (I) are prepared in the instant process from the sodium salt of simvastatin, lovastatin or an analog having a 6-methyl group by one of the following methods:

(a) adding the substrate to a growing culture of Nocardia sp. for a suitable incubation period followed by isolation, and derivatization if desired;

(b) collecting a culture of the bioconverting microorganism and contacting the collected cells with the substrate.

Cultivation of the bioconverting microorganism of the genus Nocardia sp. can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the substrate to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase and this is usually 1 or 2 days after beginning cultivation of the microorganism. The amount of the substrate added is preferably from 0.01 to 5.0% by weight of the medium, more preferably from 0.05 to 0.5%, e.g., from 0.05 to 0.1% by weight. After addition of the substrate, cultivation is continued aerobically, normally at a temperature within the ranges proposed above. Cultivation is normally continued for a period of from 1 to 2 days after addition of the substrate.

In method (b), cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with a substrate under standard conditions and determining the quantity of product obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected, preferably, are then washed with a suitable washing liquid, such as physiological saline or an appropriate buffer solution.

Contact of the collected cells of the microorganism of the genus Nocardia sp. with the substrate is generally effected in an aqueous medium, for example in a phosphate buffer solution at a pH value of from 5 to 9. The reaction temperature is preferably within the range from 20° to 45° C., more preferably from 25° to 30° C. The concentration of the substrate in the reaction medium is preferably within the range from 0.01 to 5.0% by weight. The time allowed for the reaction is preferably from 1 to 5 days, although this may vary depending upon the concentration of the substrate in the reaction mixture, the reaction temperature, the hydroxylation capacity of the microorganism (which may, of course, vary from species to species and will also, as explained above, depend upon the cultivation time) and other factors.

The microorganism useful in the novel process of this invention is of the genus Nocardia sp. (MA6455). A sample of the culture designated ATCC 53695 is available in the permanent culture collection of the American Type Culture Collection at 12301 Parklawn Drive, Rockville, Md. 20852.

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude compound to column chromatography, (for example on silica gel or alumina) and eluting the column with an appropriate eluent, especially in an HPLC apparatus.

The following examples illustrate the preparation of these compounds and, as such, are not to be construed as limiting the invention set forth in the claims appended hereto.

The composition of media employed in the following examples are listed below.

Medium A

| Component | (q/l) |
| --- | --- |
| Dextrose | 4.0 |
| Malt Extract (Difco) | 10.0 |
| Yeast Extract (Difco) | 4.0 |
| Nutrient Broth (Difco) | 4.0 |

Presterile pH adjusted to 7.0 by addition of NaOH. Dispensed at 30 ml/250 ml three baffle Erlenmeyer flask. Cotton closures; sterilized 20 minutes at 121° C.

Medium B

| Component | (q/l) |
| --- | --- |
| Dextrose | 10.0 |
| Hycase SF | 2.0 |
| Beef Extract (Difco) | 1.0 |
| Corn Steep Liquor | 3.0 |

Presterile pH adjusted to 7.0 by addition of NaOH. Dispensed at 50 ml/250 ml plain Erlenmeyer flask. Cotton closures; sterilized 20 minutes at 121° C.

EXAMPLE 1

Preparation of 6(R)-[2-[8(S)-(2,2-dimethyl-butyryloxy) -2(S)-methyl-6(S)-hydroxymethyl-1,2,6,7,8, 8a(R)-hexahydronaphthyl-1(S)]ethyl]-4(R)(hydroxy)- 3,4,5,6-tetrahydro-2H-pyran-2-one A. Culture conditions and Bioconversion A source of the MA 6455 culture, frozen vegetative mycelia, spores or a 5 mm agar plug from a well sporulated plate, was inoculated into medium A. The seed culture was grown for 24–28 hours at 27° C. while being agitated at 220 rpm. The seed culture was then transferred (2.5 ml seed/flask) to medium B. The culture was allowed to grow in the production medium for 24 hours at 27° C. and 220 rpm. Sodium 7-[1,2,6,7,8,8a(R)-hexahydro-2(S)-methyl-6(R)-methyl-8(S)-(2,2-dimethylbutyryloxy)-1(S)-naphthyl]-3(R),5(R)-dihydroxyheptanoate (sodium salt) was then added to a final concentration of 200 μg/ml. The flasks were incubated at 27° C for 40 hours after addition of the sodium salt.

B. HPLC Analysis of Broth

The whole broth from A was analyzed for metabolites of the added sodium salt 5.0 ml of the whole broth bioconversion was mixed with 5.0 ml of 50% acetonitrile/$H_2O$. The mixtures were shaken for 15 minutes on a reciprocating shaker and insoluble materials removed by centrifugation. A portion of the supernatant solution was analyzed by HPLC using the conditions described below:

HPLC Conditions for Separation of the Metabolites of the Sodium Salt

Injection Volume: 5 μl
Flow Rate: 1.1 ml/min
Detection: 237 nm; 210 nm
Column: Hamilton PRP 1 (4.1×150 mm; 5 μm)
Mobile Phases:
 A: 10% acetonitrile in 20 mM ammonium phosphate, pH 6.1
 B: 70% acetonitrile/30% $H_2O$
Temperature: 25° C.

| Time | % A | % B |
| --- | --- | --- |
| 0 | 90 | 10 |
| 3.00 | 69 | 31 |
| 5.00 | 69 | 31 |
| 11.00 | 0 | 100 |
| 13.00 | 0 | 100 |
| 13.50 | 90 | 10 |
| 18.50 | 90 | 10 |

In a typical chromatogram the 6-hydroxymethyl simvastatin derivative is detected after 10 minutes. The percent conversion of the 6-desmethyl-6-hydroxymethyl simvastatin derivative is 24% as compared to 11% when the N. autotrophica (MA6180) is used as the culture.

EXAMPLE 2

Preparation of 6(R)-[2-[8(S)-(2,2-dimethylbutyryloxy)-2(S)-methyl-6(S)-carboxy-1,2,6,7,8,8a(R)-hexahydronaphthyl-1(S)](ethyl]-4(R) (hydroxy)-3,4,5,6-tetrahydro-2H-pyran-2one A. Bioconversion The bioconversion is carried out following the conditions of example 1.

B. Purification of 6-Carboxy Fraction 100 ml of whole broth from the bioconversion in A was subjected to centrifugation to remove insoluble material. The supernatant solution was brought to pH 5.0 by the addition of a few drops of 85% phosphoric acid. This solution was then extracted with 100 ml of an ethyl acetate/hexane (80:20) mixture; the layers were separated and the pH of the aqueous layer readjusted to 5.0. The aqueous layer was then extracted with 2×100ml portions of ethyl acetate/hexane (80:20) and the ethyl acetate/hexane extracts were then discarded. The pH of the aqueous layer was reduced to 3.5 by the addition of 85% phosphoric acid and then extracted with 3×100ml portions of ethyl acetate. The ethyl acetate layers were combined and extracted with 30 ml of 1% ammonium acetate. The ammonium acetate solution was analyzed by HPLC for the 6-carboxy derivative following the conditions described for the analysis of the 6-hydroxymethyl derivatives.

C. Results

The 6-carboxy simvastatin derivative is detected at about 6 minutes. The percent conversion of the 6-carboxy simvastatin derivative was 11% which is approximately the same as when N. autotrophica (MA6181) is used as the culture.

EXAMPLE 3

Preparation of 6(R)[2-[8(S)-(2-methylbutyryloxy)-2(S)-methyl-6(S)-hydroxymethyl-1,2,6,7,8,8a(R)-hexahydronaphthyl-1(S)]ethyl]-4(R) (hydroxy)-3,4,5,6-tetrahydro-2H-pyran-2-one A. Culture Conditions and Bioconversion A source of the MA6455 culture, frozen vegetative mycelia, spores or a 5 mm agar plug from a well sporulated plate was inoculated into medium A. The seed culture was incubated for 48 hours at 27° C. while being agitated at 200 rpm. The seed culture was then transferred (2.5 ml seed/flask) to medium B and incubated as above for 24 hours. Sodium 7-[1,2,6,7,8,8a(R)-hexahydro-2(S),6(R)-dimethyl-8(S)-(2-methylbutyryloxy)-1(S)-naphthyl]-3(R),5(R)-dihydroxyheptanoate (sodium salt) was then added to a final concentration of 200 μg/ml. The reaction culture was then incubated at 27° C. and 200 rpm for 24–48 hours.

B. HPLC Analysis of Broth

The broth was analyzed as described in Example 1B. The percent conversion of the 6-desmethyl-6-hydroxymethyl lovastatin derivative was 22% as compared to 12% when the N. autotrophica (MA6180) is used as the culture.

What is claimed is:

1. A process for the preparation of a compound represented by the formula (I)

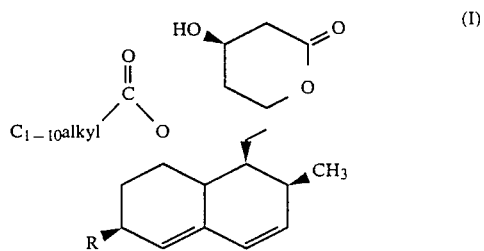

wherein:
R is $CH_2OH$ or COOH;
which comprises culturing a microorganism Nocardia sp. (MA6455) (ATCC 53695) in a nutrient medium containing assimilable sources of nitrogen and carbon and the sodium salt (II):

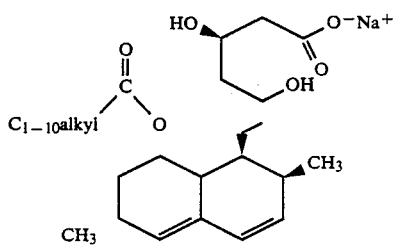

under aerobic conditions until a substantial amount of the compound is produced and isolating the compound so produced.

2. A process of claim 1 in which the culturing of the microorganism occurs at a temperature of about 27° C.

3. A process of claim 1 in which the culturing of the microorganism continues from 4 days to 6 days.

4. A process of claim 3 in which

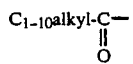

is 2-methylbutyryl or 2,2-dimethylbutyryl.

5. A process of claim 4 in which

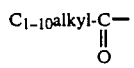

is 2,2-dimethylbutyryl.

6. A process of claim 4 in which

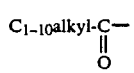

is 2-methylbutyryl.

7. A process of claim 5 in which R is $CH_2OH$.
8. A process of claim 5 in which R is COOH.
9. A process of claim 6 in which R is $CH_2OH$.

* * * * *